(12) United States Patent
Pipenhagen et al.

(10) Patent No.: US 9,282,994 B2
(45) Date of Patent: Mar. 15, 2016

(54) VASCULAR ACCESS TO CLOSURE SHEATH AND METHODS

(75) Inventors: Catherine A. Pipenhagen, Chanhassen, MN (US); Vasanth R. Shenai, Minneapolis, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 718 days.

(21) Appl. No.: 12/889,733

(22) Filed: Sep. 24, 2010

(65) Prior Publication Data

US 2011/0077598 A1 Mar. 31, 2011

Related U.S. Application Data

(60) Provisional application No. 61/245,989, filed on Sep. 25, 2009.

(51) Int. Cl.
| | | |
|---|---|---|
| A61M 5/00 | (2006.01) |
| A61B 17/34 | (2006.01) |
| A61B 17/00 | (2006.01) |
| A61M 25/00 | (2006.01) |
| A61M 25/06 | (2006.01) |
| A61B 17/04 | (2006.01) |

(52) U.S. Cl.
CPC ......... *A61B 17/3468* (2013.01); *A61B 17/0057* (2013.01); *A61M 25/0023* (2013.01); *A61M 25/0662* (2013.01); *A61B 17/3439* (2013.01); *A61B 2017/00623* (2013.01); *A61B 2017/00659* (2013.01); *A61B 2017/00663* (2013.01); *A61B 2017/00778* (2013.01); *A61B 2017/00867* (2013.01); *A61B 2017/0409* (2013.01); *A61B 2017/0417* (2013.01); *A61B 2017/3484* (2013.01); *A61M 2025/0024* (2013.01)

(58) Field of Classification Search
CPC ........... A61B 17/0057; A61B 17/3468; A61B 17/3439; A61B 2017/00659; A61B 2017/0409; A61B 2017/3484; A61B 2017/00623; A61B 2017/00663; A61B 2017/00867; A61B 2017/0417; A61B 2017/00778; A61M 25/0023; A61M 25/0662; A61M 2025/0024
USPC .............................. 604/163, 164.03, 171, 530
See application file for complete search history.

(56) References Cited

U.S. PATENT DOCUMENTS

| | | | | | |
|---|---|---|---|---|---|
| 3,185,151 | A | * | 5/1965 | Czorny | 604/163 |
| 4,601,713 | A | * | 7/1986 | Fuqua | 604/514 |
| 4,710,181 | A | * | 12/1987 | Fuqua | 604/514 |

(Continued)

OTHER PUBLICATIONS

PCT International Search Report for International Application No. PCT/US2010/002614, mailed Dec. 30, 2010 (4 pp.).

*Primary Examiner* — Gregory Anderson
*Assistant Examiner* — Son Dang
(74) *Attorney, Agent, or Firm* — Holland & Hart

(57) ABSTRACT

An insertion sheath and related methods include a tube member and a shape memory feature. The tube member defines an insertion lumen. The shape memory feature is positioned at a distal end portion of the tube member. The shape memory feature provides a monofold shape in the tube member when in a first state, and a radially expanded shape in the tube member in a second state upon application of an expansion force. The shape memory feature returns the monofold shape after removal of the expansion force. The insertion sheath may function as an access to closure sheath that is suitable for use as a procedural insertion sheath when treating the patient and a closure insertion sheath when sealing closed the vascular puncture.

26 Claims, 3 Drawing Sheets

(56) References Cited

U.S. PATENT DOCUMENTS

| | | | |
|---|---|---|---|
| 4,738,666 A * | 4/1988 | Fuqua | 604/514 |
| 4,795,426 A | 1/1989 | Jones | |
| 5,242,398 A * | 9/1993 | Knoll et al. | 604/103.05 |
| 5,738,667 A * | 4/1998 | Solar | 604/523 |
| 5,766,220 A * | 6/1998 | Moenning | 606/213 |
| 5,919,225 A * | 7/1999 | Lau et al. | 606/198 |
| 5,976,174 A | 11/1999 | Ruiz | |
| 5,997,508 A * | 12/1999 | Lunn et al. | 604/164.08 |
| 6,015,429 A * | 1/2000 | Lau et al. | 623/1.2 |
| 6,045,569 A | 4/2000 | Kensey et al. | |
| 6,090,130 A | 7/2000 | Nash et al. | |
| 6,179,863 B1 | 1/2001 | Kensey et al. | |
| 6,352,553 B1 * | 3/2002 | van der Burg et al. | 623/1.23 |
| 7,250,057 B2 * | 7/2007 | Forsberg | 606/213 |
| 7,766,820 B2 * | 8/2010 | Core | 600/140 |
| 7,780,630 B2 * | 8/2010 | Jenson et al. | 604/103.14 |
| 7,780,692 B2 * | 8/2010 | Nance et al. | 606/198 |
| 8,337,518 B2 * | 12/2012 | Nance et al. | 606/194 |
| 8,690,936 B2 * | 4/2014 | Nguyen et al. | 623/1.11 |
| 8,790,387 B2 * | 7/2014 | Nguyen et al. | 623/1.11 |
| 2004/0087968 A1* | 5/2004 | Core | 606/108 |
| 2005/0096697 A1 | 5/2005 | Forsberg et al. | |
| 2005/0125030 A1 | 6/2005 | Forsberg et al. | |
| 2005/0137499 A1* | 6/2005 | Sheets et al. | 600/562 |
| 2005/0187578 A1* | 8/2005 | Rosenberg et al. | 606/232 |
| 2007/0106330 A1* | 5/2007 | Rosenberg et al. | 606/232 |
| 2007/0244550 A1* | 10/2007 | Eidenschink | 623/1.49 |
| 2008/0234543 A1* | 9/2008 | Goldwasser | 600/37 |
| 2008/0243072 A1* | 10/2008 | Jenson et al. | 604/103.14 |
| 2008/0262302 A1 | 10/2008 | Azarbarzin et al. | |
| 2009/0216075 A1* | 8/2009 | Bell et al. | 600/37 |
| 2010/0057009 A1* | 3/2010 | McQueen et al. | 604/164.03 |
| 2010/0094392 A1* | 4/2010 | Nguyen et al. | 623/1.11 |

* cited by examiner

VASCULAR ACCESS TO CLOSURE SHEATH AND METHODS

CROSS-REFERENCE TO RELATED ED APPLICATION

This application claims the benefit of U.S. provisional patent application No. 61/245,989, filed Sep. 25, 2009, which is hereby incorporated by reference herein in its entirety.

TECHNICAL FIELD

The present disclosure relates generally to medical devices and more particularly to sheath devices for providing access through a tissue wall.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., catheters) can pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,090,130 and 6,045,569, which are hereby incorporated in their entireties by this reference.

Prior closure devices, such as the ones described in the above-mentioned patents, place an anchor inside the vessel to provide a backstop against which a sealing member that is positioned outside the vessel can be compressed. In some instances, a particular shaped insertion sheath is used to help position the anchor within the vessel. This insertion sheath may be different from the insertion sheath used for procedures related to treating the patient prior to sealing closed the vessel puncture with the vascular closure device.

SUMMARY

One aspect of the present disclosure relates to an insertion sheath that includes a tube member and a shape memory feature. The tube member defines an insertion lumen. The shape memory feature is positioned at a distal end portion of the tube member. The shape memory feature provides a monofold shape in the tube member when in a first state, and a radially expanded shape in the tube member in a second state upon application of an expansion force. The shape memory feature returns the monofold shape after removal of the expansion force.

The monofold shape may include a fold aligned parallel with a length dimension of the tube member. The shape memory features can include a Nitinol material. The shape memory feature is shaped as a band structure, wherein the band structure has a maximum band outer dimension and a minimum band inner dimension. The tube member has a maximum tube outer dimension and a minimum tube inner dimension. The maximum tube outer dimension is substantially equal to the maximum band outer dimension, and the minimum tube inner dimension being smaller than the minimum band inner dimension. The tube member can have a maximum tube outer dimension that is substantially equal to the minimum band inner dimension.

A transition member may extend from an outer surface of the shape memory feature to an outer surface of the tube member. The shape memory feature may be mounted to an exterior surface of the tube member. A hub member may extend from a proximal end portion of the tube member, wherein the hub member is configured for attachment to at least a vascular closure device.

Another aspect of the present disclosure relates to an insertion sheath that includes a tube member, a hub member, and a shape memory member. The tube member has proximal and distal end portions. The hub member is mounted to the proximal end portion of the tube member. The shape memory member is positioned at the distal end portion and includes a Nitinol material. The shape memory member has a rest state that defines a monofold feature in the distal end portion of the tube member, and an expanded state wherein the monofold feature is at least partially expanded radially outward.

The monofold feature may include at least one fold defined in the tube member, wherein the at least one fold is arranged parallel with a length dimension of the tube member. The shape memory member may have a band shape, a length, a thickness, an outer surface, and an inner surface. The thickness of the shape memory member may be less than a thickness of a sidewall of the tube member. The outer surface of the shape memory member may be arranged coplanar with an outer surface of the tube member. The shape memory member may be configured to maintain the monofold shape after returning from the expanded state to the rest state for a predetermined number of cycles from the rest state to the expanded state and back to the rest state.

A further aspect of the present disclosure relates to a method treating a patient through a percutaneous incision using an insertion sheath. The insertion sheath includes a shape memory member that defines a monofold shape in a distal end portion of the insertion sheath. The method may include inserting the insertion sheath into the percutaneous incision, and inserting a treatment instrument through the insertion sheath for treatment of the patient at a location distal of the insertion sheath, wherein inserting the treatment instrument at least partially radially expands the monofold feature. The method may also include withdrawing the treatment instrument from the insertion sheath, inserting a portion of a vascular closure device through the insertion sheath and distally beyond the monofold feature, and sealing closed the percutaneous incision with the vascular closure device.

Withdrawing the treatment instrument may permit the shape memory member to return to a rest state wherein the monofold feature is present. Inserting a portion of a vascular closure device through the insertion sheath may include advancing an anchor out of a distal end of the insertion sheath. Sealing closed the percutaneous incision includes compressing a sealing member on a side of the vessel opposite a position of the anchor. The method may further include contacting the anchor with the distal end of the insertion sheath to rotate the anchor after advancing the anchor out of the distal end of the insertion sheath.

Additional advantages and novel features will be set forth in the description which follows or can be learned by those skilled in the art through reading these materials or practicing the examples disclosed herein. The advantages of the invention can be achieved through the means recited in the attached claims.

BRIEF DESCRIPTION OF THE DRAWINGS

The accompanying drawings illustrate various embodiments of the present disclosure and are a part of the specification. The illustrated embodiments are merely examples and do not limit the scope of the invention.

Throughout the drawings, identical reference numbers designate similar, but not necessarily identical, elements.

DETAILED DESCRIPTION

Figure 1:
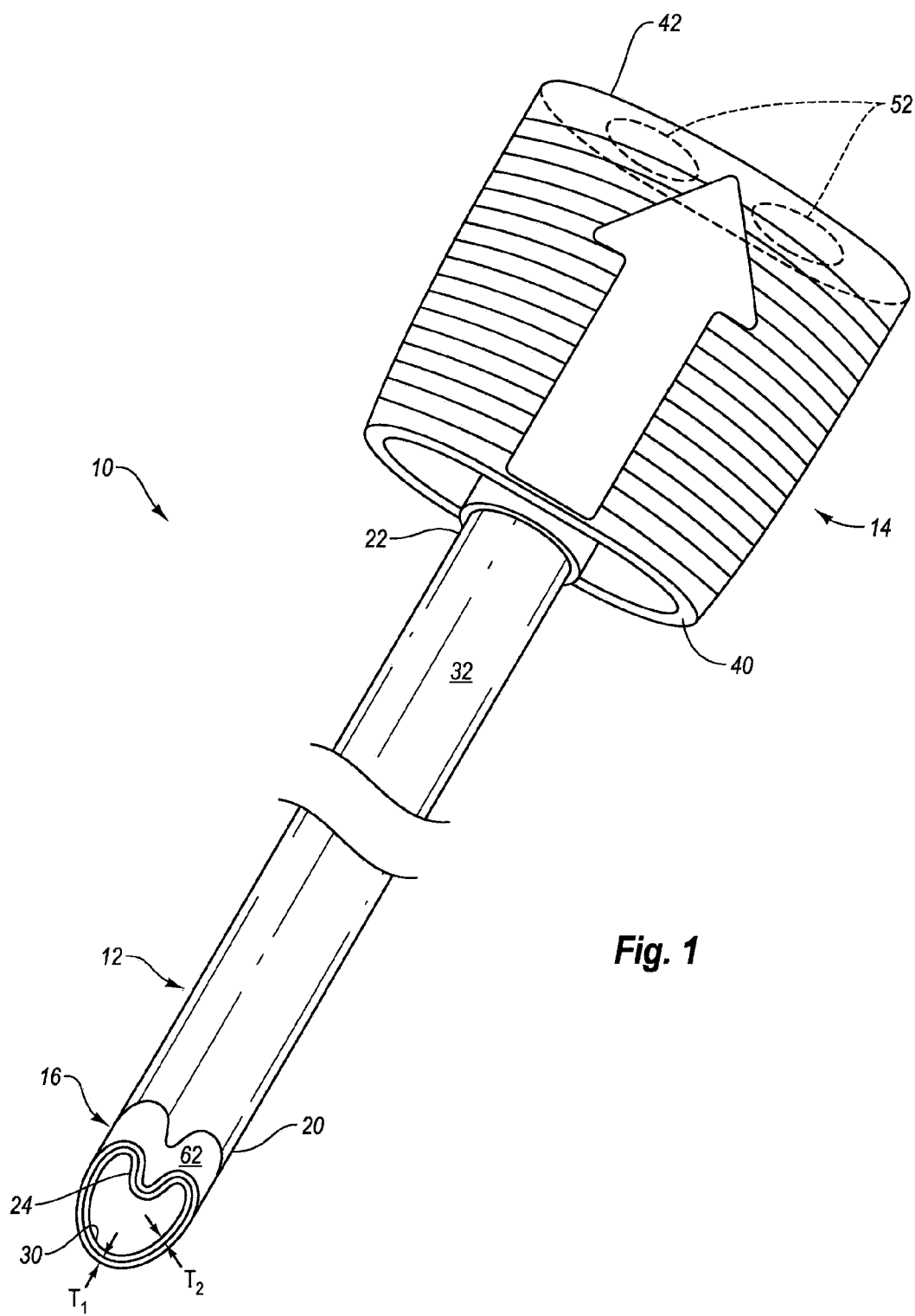
FIG. 1 is a perspective view of an example insertion sheath according to the present disclosure.

As mentioned above, vascular procedures are conducted throughout the world and require access to a vessel through a puncture. Often, the artery is a femoral artery. Typically, a procedural insertion sheath is used to provide access into the vessel through the puncture for instruments and devices used to treat the patient. Such instruments and devices may include, for example, catheters or guidewires that pass through a lumen defined by the procedural insertion sheath. The lumen size is usually maximized to provide easier passage of the procedural instruments through the procedural insertion sheath for a given puncture size.

Some types of vascular closure devices include an anchor member that is positioned within the vessel. The anchor is usually intended to remain in the vessel (intraluminal) at least while the puncture in the vessel is sealed closed. Some insertion sheaths used with such vascular closure devices include a monofold structure at a distal end of the insertion sheath. The monofold structure provides an obstruction to return passage of an anchor member into the insertion sheath after the anchor has been deployed distally from the insertion sheath. The distal end of the insertion sheath, due in part to the monofold structure, may provide a surface against which the anchor engages to rotate the anchor into a position generally parallel with the internal wall of the vessel. The anchor may then anchor against the vessel wall when the insertion sheath is retracted from the puncture.

A sheath exchange after treatment of the patient and prior to using the vascular closure device is typically required due to the differences between procedural insertion sheaths used with patient treatment instruments and closure insertions sheaths with monofold structures used with vascular closure devices. The present disclosure is directed to an insertion sheath that is configured for use both as a procedural sheath and as an insertion sheath. This type of insertion sheath is operable from the time of gaining access to the vessel prior to treating the patient, to the time of closing the vessel puncture after patient treatment is completed. The insertion sheath may be referred to as an "access to closure" insertion sheath because of its capability for use as both a procedural insertion sheath and a closure insertion sheath. The use of an access to closure insertion sheath may effectively eliminate the use of one of two insertions sheaths needed in at least some prior treatment methods when using a vascular closure device having an intraluminal positioned anchor.

In one example, the insertion sheath includes a shape memory feature at a distal end portion of the insertion sheath. The shape memory feature provides a monofold shape in the distal end portion of the insertion sheath when the insertion sheath is in a rest position. The shape memory feature permits the monofold feature to be expanded radially outward when a radially outward force is applied to the shape memory feature from within the insertion sheath. In one example, the radially outward force is applied by a procedural instrument that is inserted into the insertion sheath during treatment of the patient. After removal of the procedural instrument from the insertion sheath, the shape memory feature returns from an expanded state to the rest state to again provide the monofold feature in the distal end portion of the sheath. The shape memory feature can be configured to return the monofold feature to the sheath after multiple cycles from the rest state to the expanded state and back to the rest state. In at least one example, the number of cycles possible is in the range of about 5 to about 100 cycles from the rest state to the expanded state and back to the rest state.

The shape memory feature may include, for example, a Nitinol material. The shape memory feature may be shaped in the form of, for example, a band, loop or ring that is positioned on the insertion sheath. The shape memory feature may include radiopaque material that permits tracking of the shape memory feature inside the patient using, for example, x-ray or other visualization technology. The radiopaque feature may provide certain advantages related to viewing the shape memory feature internal the patient using, for example, fluoroscopy and X-ray techniques. The added ability to visualize a portion of the insertion sheath from external the patient may provide a position indicator for the operator that the insertion sheath is properly positioned in the vessel in addition to blood flashback and tactile sensing (via the anchor within the vessel). Some example "access to closure" insertion sheaths are described in further detail below with reference to the attached figures.

As used in this specification and the appended claims, the term "engage" and "engagable" are also used broadly to mean interlock, mesh, or contact between two devices. Likewise "disengage" or "disengageable" means to remove or capable of being removed from interlock, mesh, or contact. A "sheath" is an elongated device with a passageway. The passageway may be enclosed or open (e.g., a trough). A "lumen" refers to any open space or cavity in a bodily organ, especially in a blood vessel. "Slidingly mounted" means movable relative to an appropriate support. The words "including" and "having," as used in the specification, including the claims, have the same meaning as the word "comprising."

Referring now to the drawings, and in particular to FIGS. 1-5, an example insertion sheath 10 is shown and described. The insertion sheath 10 includes a tube member 12, a hub member 14, and a shape memory member 16. The insertion sheath 10 is adapted and configured for insertion through a percutaneous incision 82 and a vascular incision 84 of a patient (see FIG. 3). The insertion sheath 10 defines an inner lumen through which treatment devices and instruments may pass into a vessel 76 for treatment of the patient.

The tube member 12 includes a distal end portion 20, a proximal end portion 22, and a monofold structure 24. The monofold structure 24 may include at least one fold arranged parallel with a longitudinal axis $A_1$ of the tube member 12 (see FIG. 3). Various fold constructions are possible including, for example, C-shaped, V-shaped, partial fold (i.e., where facing surfaces of the fold remain out of contact with each other), and full fold (i.e., where facing surfaces of the fold contact each other). The fold construction of the monofold structure 24 shown in the figures is generally C-shaped, but may have other constructions in alternative arrangements.

The tube member 12 may also include an inner surface 30, an outer surface 32, a thickness $T_1$, a minimum internal diameter or dimension $D_1$, and a maximum outer diameter or dimension $D_2$. The minimum and maximum diameters $D_1$, $D_2$ are identified in the cross-sectional view of FIG. 5. The dimensions $D_1$ and $D_2$ are measured when the monofold structure 24 has been expanded radially outward thereby reflecting the maximum inner diameter and maximum outer diameter of the tube member 12. The maximum internal diameter $D_1$ represents the maximum size of a procedural instrument that may be inserted through the tube member 12 for treatment of the patient.

The hub member 14 includes a distal end 40, a proximal end 42, and at least one connector opening 52. The connector openings 52 may be defined in the proximal end 42 for use in, for example, attachment to a vascular closure device such as the vascular closure device disclosed in U.S. Pat. No. 7,250,057, which is hereby incorporated in its entirety by this reference. The connector openings 52 may have an shape and size needed to connection to, insertion of, or mounting of, for example, a vascular closure device or a procedural device used with the insertion sheath 10.

Other hub member configurations that may be used include additional side ports, connector openings, coupling member, or the elimination of any of these features.

The shape memory member 16 includes an inner surface 60, an outer surface 62, a distal edge 64, a proximal edge 66. When in a radially expanded state as shown in at least FIGS. 2, 2A, 4 and 5, the inner surface 60 defines a maximum internal diameter or dimension $D_3$, the outer surface 62 defines a maximum outer diameter or dimension $D_4$ and a thickness $T_2$ is defined between the outer and inner surfaces 60, 62. Shape memory member 16 may also have a length $L_1$ measured between the distal and proximal edges 64, 66.

The shape memory member 16 defines a monofold structure when in a rest state. A "rest state" is defined as a state in which no forces (or substantially no forces) are applied to the shape memory member in either the radial or axial direction. When the shape memory member 16 is positioned on the tube member 12, the monofold shape defined by the shape memory member 16, as shown in at least FIGS. 1 and 3, causes a shape of the tube member to also include a similar monofold structure.

Typically, the shape memory member 16 comprises a flexible material wherein the monofold shape of shape memory member 16 may be changed into a different shape (e.g., flexed radially outward into a generally cylindrical shape having a circular cross-section as shown in FIGS. 2, 2A, 4 and 5), and then returned back to the original monofold shape after application of the force is removed.

Figure 5:
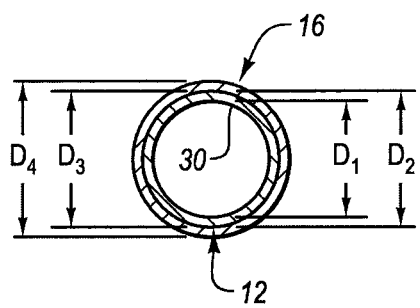
FIG. 5 is a cross-sectional view of the insertion sheath of FIG. 4.
Figure 6:
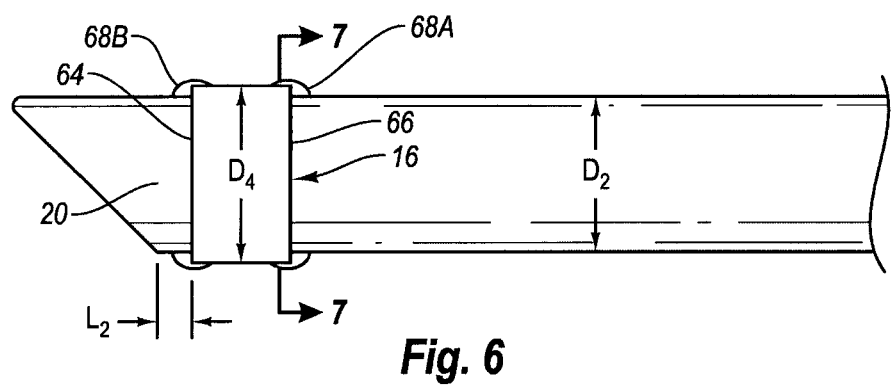
FIG. 6 is a side view of a portion of another example insertion sheath according to the present disclosure.

The insertion sheath 10 shown and described with reference to FIGS. 1-6 includes a shape memory member 16 that is positioned on or otherwise mounted to the distal end portion 20 of the tube member 12. Shape memory member 16 may be mounted to the tube member 12 using, for example, a swaging technique wherein the outer surface 62 is positioned substantially flush mounted with the outer surface 32 of that portion of tube member 12 arranged axially adjacent to one of the distal and proximal edges 64, 66. That portion of the tube member 12 that is surrounded or enclosed by the shape memory member 16 is positioned radially inward from the inner and outer surfaces 60, 62 of the shape memory member 16. FIGS. 5 and 6 illustrate a configuration in which the shape memory member 16 is swaged onto the distal end portion 20 of the tube member 12.

Figure 7:
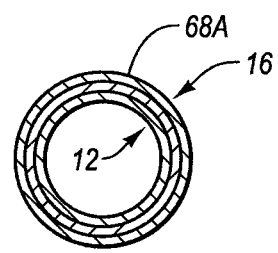
FIG. 7 is a cross-sectional view of the insertion sheath of FIG. 6.

In other embodiments, such as the embodiments of FIGS. 6 and 7, the shape memory member 16 is mounted to the outer surface 32 of the tube member 12 using, for example, an adhesive or bonding agent. The shape of the distal end portion 20 of the tube member 12 remains unchanged in the area where the shape memory member 16 is mounted to the tube member 12. Transition portions 68A, 68B may be used to transition from the outer surface 32 of the tube member 12 to the outer surface 62 of the shape memory member 16. The transition portions 68A-B may cover up the distal and proximal edges 64, 66 of the shape memory member 16 that might otherwise be exposed for inadvertent engagement when the insertion sheath 10 passes through the percutaneous incision 82 and vascular incision 84. FIG. 7 illustrates the cross-sectional view of the shape memory member 16 with transition portions 68A shown in FIG. 6.

The shape memory member 16 may be mounted to the tube member 12 using other connection methods, such as, for example, heat welding, sonic welding, co-molding, and an interference fit. In one example, an outer surface of the tube member 12 has a reduced thickness using, for example, grinding, wherein the reduced thickness portion of the tube member 12 corresponds to the shape and position for the shape memory member 16. In some embodiments, the shape memory member 16 may be mounted to the inner surface 30 of the tube member 12, as opposed to the outer surface 32.

The dimensions of the shape memory member 16 may be varied to alter the flexibility characteristics of the shape memory member 16. For example, any one of the thickness $T_2$, length $L_1$, and diameters $D_3$, $D_4$ may be changed to influence the ease in which the shape memory member 16 provides the monofold shape in the distal end portion 20 of the tube member 12, permits flexing of the shape memory member 16 from the monofold shape to the radially expanded shape, and permits return flexing back to the monofold shape.

The location of the shape memory member 16 may also be changed relative to the tube member 12. FIG. 6 illustrates the distal edge 64 of the shape memory member 16 spaced a distance $L_2$ from the distal most edge of the tube member 12. In at least some embodiments, the monofold shape of the shape memory member 16 may provide a monofold shape in the tube member 12 from at least the proximal edge 66 of the shape memory member 16 to the distal most point of the tube member 12. The distal edge 64 of the shape memory member 16 may be spaced a distance $L_2$ from the distal edge 64 of the shape memory member 16.

In one example, the diameter $D_4$ is in the range of about 0.08 inches (0.2 mm) to about 0.15 inches (0.38 mm) and the thickness $T_2$ is in the range of about 0.002 inches (0.005 mm) to 0.005 inches (0.013 mm). The length $L_1$ may be, for example, in the range of about 0.03 inches (0.076 mm) to about 0.15 inches (0.38 mm). Many other shapes and sizes for the shape memory member 16 are possible.

Figures 2, 2A, 3:
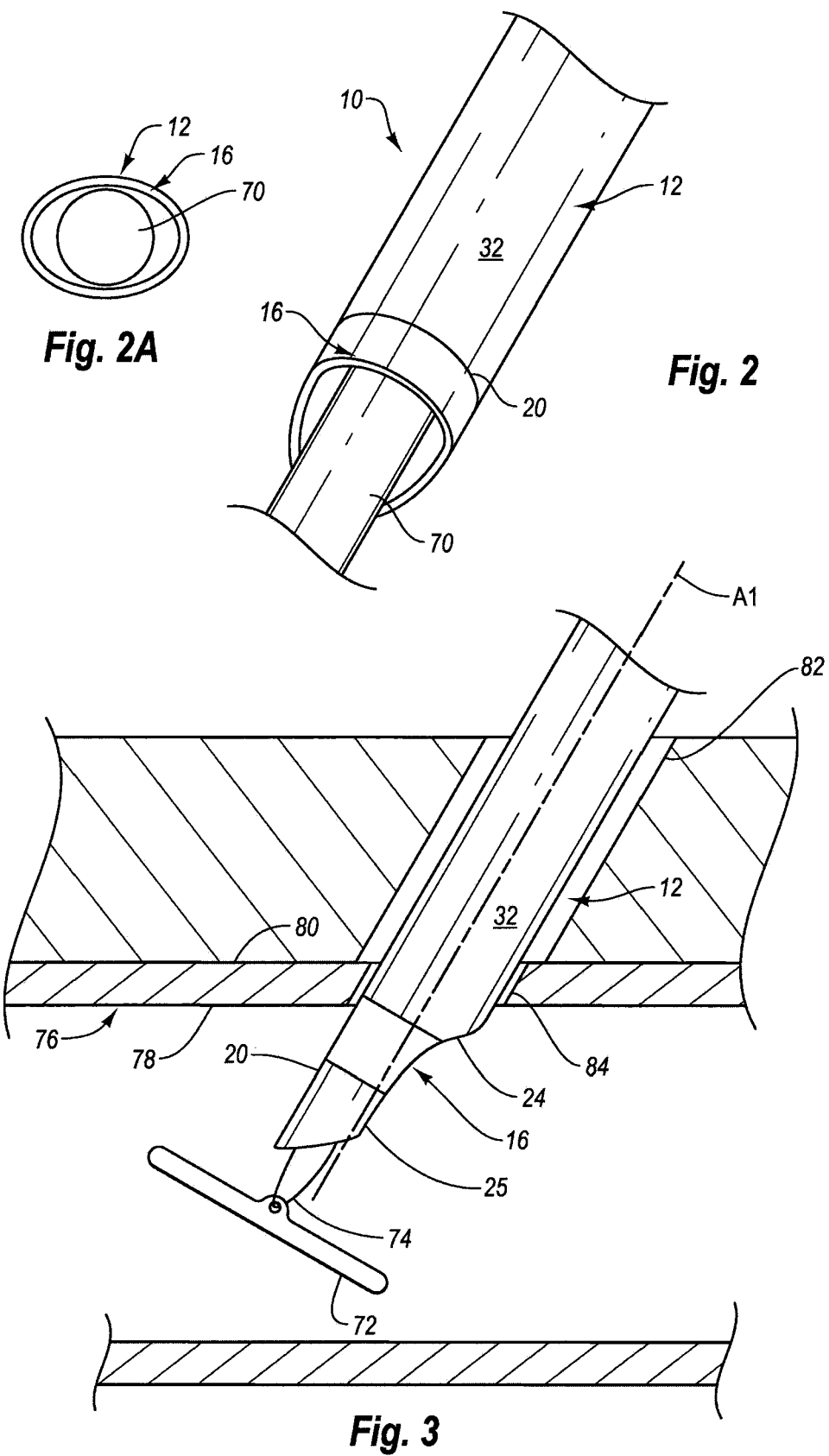
FIG. 2 is a perspective view of a portion of the insertion sheath of FIG. 1 with a procedural instrument extending from a distal end of the insertion sheath.
FIG. 2A is an end view of the insertion sheath and procedural instrument of FIG. 2.
FIG. 3 is a perspective view of a portion of the insertion sheath of FIG. 1 with a monofold at a distal end thereof and an anchor of a vascular closure device positioned adjacent to a distal end of the insertion sheath.
Figure 4:
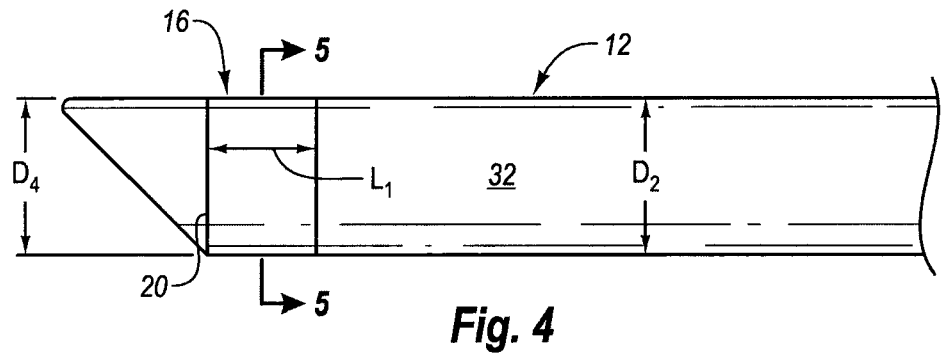
FIG. 4 is a side view of a portion of the insertion sheath of FIG. 1.

As described above, the insertion sheath 10 having a monofold shape memory member 16 may function as both a procedural insertion sheath and an insertion sheath used with a vascular closure device. FIG. 2 illustrates the insertion sheath 10 having a treatment instrument 70 extending therethrough. Insertion of treatment instrument 70 through the tube member 12 and shape memory member 16 applies a radially outward directed force that changes the shape of the shape memory member 16 from the monofold shape shown in FIG. 1 to the generally cylindrical shape having a circular cross-section shown in FIG. 2. The treatment instrument 70 has an outer dimension (e.g., an outer diameter) that is substantially equal to the dimension $D_1$ of the tube member 12, such that the shape memory member 16 is nearly completely expanded radially outward. In other embodiments, the size of the treatment instrument 70 may be smaller so that the monofold shape of the shape memory member 16 is only partially expanded radially outward.

After treatment of the patient using the treatment instrument 70, the treatment instrument 70 may be withdrawn proximally out of the insertion sheath 10. Upon withdrawal of the treatment instrument 70 proximally past the shape memory member 16, the shape memory member 16 may return back to the monofold shape shown in FIG. 1 to create a monofold in the distal end portion 20 of the tube member 12. Inclusion of the monofold shape in the insertion sheath 10 makes the insertion sheath 10 particularly useful as an insertion sheath for a vascular closure device. Many vascular closure devices include an anchor member 72 that is advanced distally out of the end of the insertion sheath as shown in FIG. 3 so that the anchor 72 is positioned within the vessel 76. The anchor 72 is coupled to remaining portions of the vascular closure device via a suture 74. Once the anchor 72 is within the vessel 76, the anchor 72 rotates from an orientation generally parallel with the longitudinal axis $A_1$ to an orientation generally perpendicular to the axis $A_1$ as shown in FIG. 3. The anchor 72 may be rotated into the generally perpendicular orientation (also defined as an orientation generally parallel with an inner wall surface 78 of the vessel 76) by pulling on the suture 74 in a proximal direction until the anchor 72 engages against the distal end portion 20 and the monofold structure 24 of the insertion sheath 10. The monofold structure 24 in the distal end portion 20 substantially limits the ability of the anchor 72 to return back into the insertion sheath 10.

With the anchor 72 arranged in the vessel 76 as shown in FIG. 3, the insertion sheath 10 may be withdrawn in a proximal direction so that the anchor 72 can engage against the inner wall surface 78. The anchor 72 can serve as an anchor against which a sealing plug of the vascular closure device (not shown) may be compressed against an opposite side of the vascular incision 84. Other details concerning use of a vascular closure device and its interaction with an insertion sheath are described in, for example, U.S. Pat. No. 7,250,057, which is incorporated herein by reference.

Various materials may be used for the shape memory member 16. In at least one example, the shape memory member 16 includes a shape memory Nitinol material or other shape memory material. In one example, the shape memory member 16 includes platinum iridium as an additive in the amount of, for example, 2-3% by volume to provide at least some visibility of the shape memory member 16 using X-ray or other technology. Some types of Nitinol materials are especially effective at retaining a particular original shape while having flexibility that permits deformation away from the original shape upon application of a force, and the ability to return to the original shape once that force is removed.

The option of using a single insertion sheath for both a procedural insertion sheath as well as an insertion sheath for use with a vascular closure device may provide savings in time as well as reduction in costs and complexity in treating a patient. As discussed above, when a separate monofold insertion sheath is required for a vascular closure procedure, the procedural insertion sheath must be exchanged for the monofold insertion sheath after the treatment procedure on the patient has been completed. An insertion sheath exchange may be time-consuming, may result in complications, and requires additional devices that altogether increase the complexity as well as the cost associated with treating the patient. The example insertion sheaths described herein may address these and other issues. Furthermore, the example insertion sheaths described herein may be used with other procedures and at other locations in a patient. The disclosure herein should not be limited to percutaneous incisions, vascular incisions, or vascular closure devices.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:

1. An insertion sheath, comprising:
   a tube member defining an insertion lumen, the tube member having a longitudinal axis;
   a shape memory feature positioned at a distal end of the tube member, the shape memory feature comprising a band, the shape memory feature providing a monofold shape in the tube member in a first state, the monofold shape including at least one fold arranged in parallel with the longitudinal axis of the tube, and a radially expanded shape in the tube member in a second state upon application of an expansion force, the shape memory feature being able to return to the monofold shape after removal of the expansion force.

2. The insertion sheath of claim 1, wherein the monofold shape includes a fold aligned parallel with a length dimension of the tube member.

3. The insertion sheath of claim 1, wherein the shape memory feature comprises Nitinol material.

4. The insertion sheath of claim 1, wherein the band has a maximum band outer dimension and a minimum band inner dimension.

5. The insertion sheath of claim 4, wherein the tube member has a maximum tube outer dimension and a minimum tube inner dimension, the maximum tube outer dimension being substantially equal to the maximum band outer dimension, and the minimum tube inner dimension being smaller than the minimum band inner dimension.

6. The insertion sheath of claim 4, wherein the tube member has a maximum tube outer dimension that is substantially equal to the minimum band inner dimension.

7. The insertion sheath of claim 6, further including a transition member extending from an outer surface of the shape memory feature to an outer surface of the tube member.

8. The insertion sheath of claim 1, further comprising a hub member extending from a proximal end portion of the tube member, the hub member configured for attachment to at least a vascular closure device.

9. The insertion sheath of claim 1, wherein the shape memory feature is mounted to the distal end portion of the tube member.

10. The insertion sheath of claim 1, wherein the shape memory feature is fixed to the tube member.

11. The insertion sheath of claim 1, wherein the shape memory feature changes a shape of the tube member between the first and second states.

12. The insertion sheath of claim 1, wherein providing the monofold in the tube member includes forming the monofold shape in a sidewall of the tube member.

13. An insertion sheath, comprising:
a tube member having proximal and distal end portions and a longitudinal axis;
a hub member mounted to the proximal end portion of the tube member;
a shape memory member positioned at the distal end, the shape memory member comprising a loop structure, the shape memory member including Nitinol material, the shape memory member having a rest state that defines a monofold feature in the distal end portion of the tube member, the monofold shape including at least one fold arranged in parallel with the longitudinal axis of the tube, and an expanded state wherein the monofold feature is at least partially expanded radially outward.

14. The insertion sheath of claim 13, wherein the monofold feature includes at least one fold defined in the tube member and aligned longitudinally with a length dimension of the tube member.

15. The insertion sheath of claim 14, wherein the at least one fold comprises a C-shape.

16. The insertion sheath of claim 13, wherein shape memory member having has a length, a thickness, an outer surface, and an inner surface.

17. The insertion sheath of claim 16, wherein the shape memory member has a thickness that is less than a thickness of a sidewall of the tube member.

18. The insertion sheath of claim 13, wherein the shape memory member is configured to maintain the monofold feature after returning from the expanded state to the rest state for a predetermined number of cycles from the rest state to the expanded state and back to the rest state.

19. An insertion sheath, comprising:
a tube member defining an insertion lumen;
a shape memory feature positioned at a distal end portion of the tube member, the shape memory feature providing a monofold shape in the tube member in a first state, and a radially expanded shape in the tube member in a second state upon application of an expansion force, the shape memory feature being able to return to the monofold shape after removal of the expansion force;
wherein the shape memory feature is mounted to an exterior surface of the tube member.

20. The insertion sheath of claim 19, wherein the monofold shape includes a fold aligned parallel with a length dimension of the tube member.

21. The insertion sheath of claim 19, wherein the shape memory feature comprises Nitinol material.

22. An insertion sheath, comprising:
a tube member having proximal and distal end portions;
a hub member mounted to the proximal end of the tube member;
a shape memory member positioned at a distal end of the distal end portion, the shape memory member including Nitinol material, the shape memory member having a rest state that defines a monofold feature in the distal end portion of the tube member, and an expanded state wherein the monofold feature is at least partially expanded radially outward;
wherein the shape memory member has a band shape with a length, a thickness, an outer surface, and an inner surface, and the outer surface of the shape memory member is arranged coplanar with an outer surface of the tube member.

23. An insertion sheath, comprising:
a tube member defining an insertion lumen;
a shape memory feature positioned at a distal end of the tube member, the shape memory feature providing a monofold shape in the tube member in a first state, and a radially expanded shape in the tube member in a second state upon application of an expansion force, the shape memory feature being able to return to the monofold shape after removal of the expansion force;
wherein the shape memory feature is shaped as a band structure, the band structure having a maximum band outer dimension and a minimum band inner dimension, and the tube member has a maximum tube outer dimension and a minimum tube inner dimension, the maximum tube outer dimension being substantially equal to the maximum band outer dimension, and the minimum tube inner dimension being smaller than the minimum band inner dimension.

24. An insertion sheath, comprising:
a tube member defining an insertion lumen;
a shape memory feature positioned at a distal end portion of the tube member, the shape memory feature providing a monofold shape in the tube member in a first state, and a radially expanded shape in the tube member in a second state upon application of an expansion force, the shape memory feature being able to return to the monofold shape after removal of the expansion force;
wherein the shape memory feature is shaped as a band structure, the band structure having a maximum band outer dimension and a minimum band inner dimension, and the tube member has a maximum tube outer dimension that is substantially equal to the minimum band inner dimension.

25. The insertion sheath of claim 24, further comprising a transition member extending from an outer surface of the shape memory feature to an outer surface of the tube member.

26. An insertion sheath, comprising:
a tube member having proximal and distal end portions;
a hub member mounted to the proximal end portion of the tube member;
a shape memory member positioned at a distal end of the distal end portion, the shape memory member including Nitinol material, the shape memory member having a rest state that defines a monofold feature in the distal end portion of the tube member, and an expanded state wherein the monofold feature is at least partially expanded radially outward;
wherein the shape memory member has a band shape, the shape memory member having a length, a thickness, an outer surface, and an inner surface, the thickness being less than a thickness of a sidewall of the tube member.

* * * * *